US00PP37232P2

(12) United States Plant Patent
Vlachos

(10) Patent No.: US PP37,232 P2
(45) Date of Patent: Jan. 27, 2026

(54) ***TECOMA* PLANT NAMED 'TEC60109107'**

(50) Latin Name: *Tecoma stans.*
Varietal Denomination: TEC60109107

(71) Applicant: New Plant Introductions, LLC, Mesa, AZ (US)

(72) Inventor: Demetrios Vlachos, Mesa, AZ (US)

( * ) Notice: Subject to any disclaimer, the term of this patent is extended or adjusted under 35 U.S.C. 154(b) by 0 days.

(21) Appl. No.: 18/915,650

(22) Filed: Oct. 15, 2024

(51) Int. Cl.
*A01H 6/00* (2018.01)
*A01H 5/00* (2018.01)
*A01H 5/02* (2018.01)

(52) U.S. Cl.
USPC ..... Plt./226

CPC ..... *A01H 6/00* (2018.05); *A01H 5/02* (2013.01)

(58) Field of Classification Search
USPC ..... Plt./226
See application file for complete search history.

(56) References Cited

U.S. PATENT DOCUMENTS

PP24,169 P2 * 1/2014 Hull ..... A01H 6/00 Plt./226

* cited by examiner

*Primary Examiner* — Karen M Redden
(74) *Attorney, Agent, or Firm* — Accelerate IP LLC

(57) ABSTRACT

A new cultivar of *Tecoma* plant named 'TEC60109107' that is characterized by reddish-orange flowers, a compact habit. and self cleaning flowers.

2 Drawing Sheets

Botanical classification: *Tecoma stans.*
Variety denomination: 'TEC60109107'.

BACKGROUND OF THE INVENTION

The present invention relates to a new and distinct cultivar of *Tecoma* plant botanically known as *Tecoma* and hereinafter referred to by the cultivar name 'TEC60109107'.

'TEC60109107' originated in 2023 from a mutation which manifested a unique characteristic that distinguished it from *Tecoma* 'Sparky' plant (not patented) discovered by the Inventor in Queen Creek, Arizona. The new *Tecoma* emerged as a single flowering specimen displaying distinct traits, included a compact growth habit, attractive flowers, and enhanced temperature tolerance. The resulting seeds were subsequently planted and grown.

Asexual reproduction of the new cultivar 'TEC60109107' first occurred by taking cuttings of herbaceous shoots of the 'Sparky' *Tecoma* plant in 2023 in Queen Creek, Arizona. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Tecoma* cultivar 'TEC60109107'. These traits in combination distinguish 'TEC60109107' as a new and distinct cultivar apart from other existing known varieties of *Tecoma*.

*Tecoma* 'TEC60109107' exhibits reddish-orange flowers.

*Tecoma* 'TEC60109107' exhibits a compact growth habit.

*Tecoma* 'TEC60109107' exhibits enhanced temperature tolerance.

The closest comparison cultivar is *Tecoma* 'Sparky' (not patented) by the following characteristics:

'TEC60109107' has a more compact habit than 'Sparky'.

'TEC60109107' has reddish-orange flowers. The flowers of *Tecoma* 'Sparky' are yellow with orange throat.

'TEC60109107' is distinguishable from *Tecoma* 'Sparky' by its flower colors. The *Tecoma* 'Sparky' is a more abrupt transition from throat to petal color, while the 'TEC60109107' is a gradual transition from throat to petal color. The *Tecoma* 'Sparky' has a deeper red throat and more vibrant yellow while the 'TEC60109107' has a paler reddish-orange throat that gradually leads to the yellow petals.

BRIEF DESCRIPTION OF THE DRAWINGS

The accompanying photographs illustrates the distinguishing traits of *Tecoma* 'TEC60109107'. The plant in the photographs show an overall view and a closeup view of a 30 month old plant.

The photographs were taken with conventional techniques and although colors may appear different from actual colors due to light reflectance it is as accurate as possible by conventional photograph techniques.

BOTANICAL DESCRIPTION OF THE PLANT

The following is a detailed description of the new *Tecoma* cultivar named 'TEC60109107'. Data was collected in Queen Creek, Ariz. from 12-month-old outdoor grown plants in 3 gallon containers. The time of year was Summer and the temperature range was 26-37 degrees Centigrade during the day and 15-21 degrees Centigrade at night. Color determinations are in accordance with the Pantone color system, except where general color terms of ordinary dictionary significance are used. The growing requirements are similar to the species. 'TEC60109107' has not been tested under all possible conditions and phenotypic differences may be observed with variations in environmental, climatic, and cultural conditions, however, without any variation and genotype.

Botanical classification: Bignoniaceae, *Tecoma stans* 'TEC60109107'.

Parentage: 'TEC60109107' is the product of a *Tecoma* female or seed parent *Tecoma* 'Orange Jubilee' (not patented) (*Tecoma stans* x *Tecoma alata*) and *Tecoma* 'Sparky' (*Tecoma stans*).

Vigor: Vigorous.

Growth habit: Upright.

Plant type: Perennial shrub.

Plant shape: Example slight inverted triangle.

Suitable container size: 3 gallons or 30.5 cm Cache.

Height: 7 cm-15 cm.

Width: 7 cm-10 cm.

Low temperature tolerance: 28° Fahrenheit.

High temperature tolerance: 116° Fahrenheit.

Propagation: Cuttings.

Time to initiate roots in summer: 4 Weeks.

Time to initiate roots in winter: 7 Weeks.

Time to produce a rooted cutting or liner in winter: 6-8 weeks.

Time to produce a rooted cutting or liner in summer: 4-6 weeks.

Crop time: Approximately 12 weeks.

Root system: Dicot Root System.

Stem:

*Lateral branch diameter.*—3.175 mm diameter.

*Lateral branch length.*—1.5875 mm in length.

*Internode length.*—1.905 cm.

*Stem shape.*—Round. Stem strength — Strong.

*Stem color.*—Young stems 144A, mature stems N199A.

*Pubescence.*—Absent.

Foliage:

*Leaf arrangement.*—Opposite.

*Compound or single.*—Compound.

*Number of leaves per lateral branch.*—7.

*Quantity of leaflets per leaf.*—5.

*Leaflet shape.*—Pinnate.

*Leaflet apex.*—Acute.

*Leaflet base.*—Attenuate.

*Terminal leaf dimensions.*—5 cm in length and 2.5 cm in width. Terminal leaf dimensions refer specifically to the measurements of the end leaflet (terminal leaflet) in a compound leaf, not the entire compound leaf structure with all its leaflets.

*Leaflet dimensions.*—1.3 cm in length and 3.175 cm in width.

*Texture.*—Flat/smooth both sides.

*Pubescence.*—None.

*Leaflet margin.*—Slightly Serrate.

*Venation pattern.*—Actinodromous Imperfect Marginal.

*Young leaf color* (*upper surface*).—378U.

*Young leaf color* (*lower surface*).—378U.

*Mature leaf color* (*upper surface*).—378U.

*Mature leaf color* (*lower surface*).—378U.

*Vein color* (*under surface*).—2297U.

*Leaflet attachment.*—Petiolate.

*Petiole dimensions.*—3.5 cm. in length and 2 mm. in diameter.

*Petiole color.*—2297U.

*Durability of foliage to stress.*—Good.

Flower:

*Inflorescence arrangement.*—Indeterminate.

*Inflorescence dimensions.*—20 mm in height and 15 mm in width.

*Quantity of flowers per inflorescence.*—18.

*Quantity of flowers per lateral stem.*—1.

*Quantity of flowers and buds per plant.*—8.

*Natural flowering season.*—Spring and Fall.

*Fragrance.*—None.

*Flower bud length.*—19 mm to 57.15 mm.

*Flower bud diameter.*—9.5 mm to 16 mm.

*Flower bud shape.*—Tubular.

*Bud color.*—Red Orange, 6021U.

*Lower sepal.*—Color is 161-15 C.

*Upper sepal.*—Color is 1795 CP.

*Sepal size.*—1 mm long and 1 mm wide (at its widest part).

*Sepal shape.*—Apex: Acute. Base: Cuneate with receptacle.

*Sepal texture.*—Sepals with a somewhat lustrous surface that appears moist but is dry to the touch; texture is firm, and slightly porous.

*Sepal margins.*—Sepal margins entire, lobes short, triangular, and persistent.

*Flower aspect.*—Outward.

*Flower shape.*—Trumpet Shaped; Sepals are present and are 0.635 cm in length and 0.158 cm in width; Apex is acute; Base is fused; Sepal color is 7495C.

*Flower dimensions.*—8 cm diameter and 5 cm height.

*Flower longevity.*—4 to 6 weeks.

*Number of petals.*—6.

*Fused or unfused.*—Fused.

*Petal shape.*—Triangular.

*Petal length.*—5 cm.

*Petal width.*—2 cm.

*Petal color when opening* (*upper side*).—7413C, Mango.

*Petal color when opening* (*under side*).—7600C Burnt Orange, Rimmed by Mango.

*Petal color fully opened* (*upper side*).—Distal end is 7413C; Throat is 2429C; Mango with Red/Orange Throat.

*Petal color fully opened* (*under side*).—145C Burnt Orange rimmed by Mango.

*Self-cleaning or persistent.*—Self-cleaning.

Calyx:

*Calyx dimensions.*—9.525 mm in height and 13 mm in diameter.

Peduncle:

*Peduncle dimensions.*—9 mm. in length and 1 mm. in diameter.

*Peduncle angle.*—90 degrees from vertical.

*Peduncle strength.*—Strong. Peduncle color — 146D.

Reproduction organs:

*Stamen number.*—4.

*Anther length.*—95 mm.

*Anther color.*—9B.

*Amount of pollen.*—Medium amount of pollen relative to other species within the *Tecoma* genus.

*Pistil number.*—1.

*Pistil length.*—3.5 cm.

*Stigma shape.*—Spatulate.

*Stigma color.*—Yellow. 127U.

*Style length.*—22 mm.

*Style color.*—Yellow. 127U.

*Ovary color.*—Pale Green. 377U.

Seeds:

*Quantity of seeds per pod.*—25-35 per pod.

*Seed dimensions.*—90 mm. in length and 5 mm in width.

*Seed color.*—383U.

Disease and pest resistance: Disease and pest resistance has not been observed.

Seed pod:

*Seed pod dimension.*—10-12 mm wide and 125 mm long.

*Seed pod texture.*—Smooth.

*Seed pod color.*—383U.

*Seed pod apex.*—Acute.

*Seed pod base.*—Attenuate.

COMPARISON WITH THE PARENT AND RELATED PLANTS

Plants of the new cultivar *Tecoma* 'TEC60109107' are similar to the seed parent, *Tecoma* 'Sparky' in most horticultural characteristic. However, 'TEC60109107' differs from the seed parent in the following characteristics:

The flowers of the 'TEC60109107' gradually transition from throat to petal color, whereas the flowers of *Tecoma* 'Sparky' exhibit a more abrupt transition from throat to petal color.

The 'TEC60109107' flower colors are a paler reddish-orange throat that gradually leads to yellow petals, whereas the *Tecoma* 'Sparky' has a deeper red throat and more vibrant yellow petals.

The 'TEC60109107' flower has a more compact growth habit and smaller flower structure than the *Tecoma* 'Sparky'.

'TEC60109107' shares several morphological characteristics with commercial cultivar *Tecoma* Plant Name 'TEC60109105' (U.S. Plant Pat. No. 24,169) including a similar compact size, leaf shape, growth habit and blooming season. The primary distinction is in the flower color and size: 'TEC60109105' has deep orange-red petals with red margins and yellow throats, while 'TEC60109107' has uniform mango-orange petals throughout. 'TEC60109107' also produces slightly larger flowers (2.5 inches vs. 2.2 inches) and more flowers per cluster (8-12 vs. 6-10). All other characteristics including hardiness, drought tolerance, and growth requirements are similar to 'TEC60109105'.

I claim:

1. A new and distinct variety of *Tecoma* plant named 'TEC60109107' as described and illustrated.

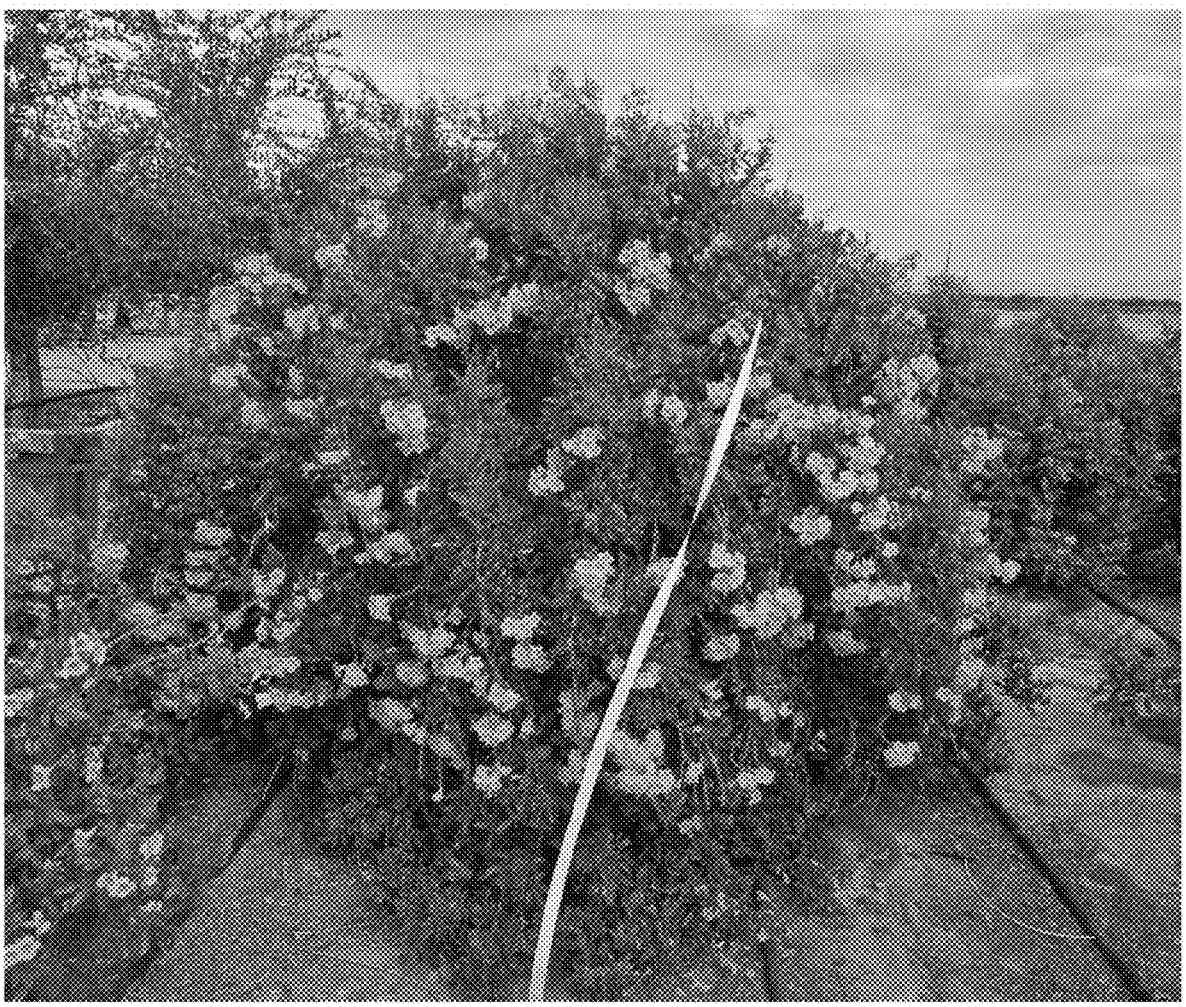

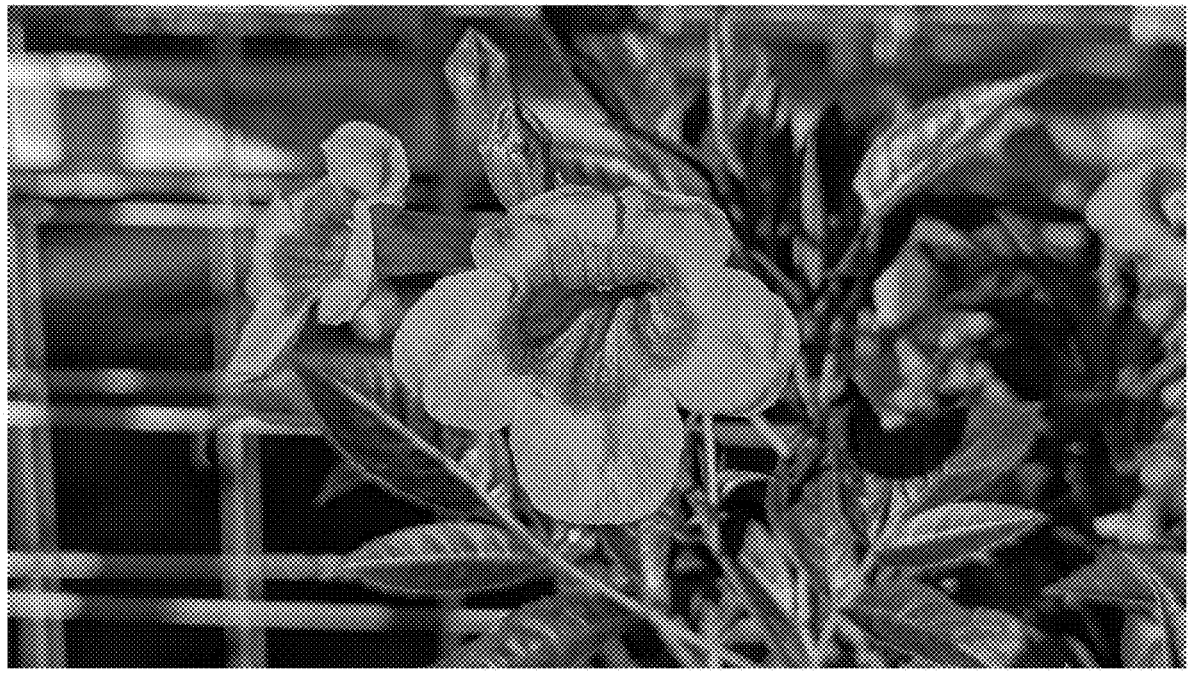

* * * * *